United States Patent
Popinchalk

(10) Patent No.: US 11,305,023 B2
(45) Date of Patent: Apr. 19, 2022

(54) METHOD FOR DIAGNOSTICALLY IMAGING LESIONS IN THE PERIPHERAL NERVOUS SYSTEM

(71) Applicant: Sam Popinchalk, Philadelphia, PA (US)

(72) Inventor: Sam Popinchalk, Philadelphia, PA (US)

( * ) Notice: Subject to any disclaimer, the term of this patent is extended or adjusted under 35 U.S.C. 154(b) by 1063 days.

(21) Appl. No.: 13/675,306

(22) Filed: Nov. 13, 2012

(65) Prior Publication Data

US 2013/0121928 A1     May 16, 2013

Related U.S. Application Data

(60) Provisional application No. 61/558,805, filed on Nov. 11, 2011.

(51) Int. Cl.
*A61K 49/00* (2006.01)
*A61K 49/16* (2006.01)

(52) U.S. Cl.
CPC .......... *A61K 49/0002* (2013.01); *A61K 49/16* (2013.01)

(58) Field of Classification Search
None
See application file for complete search history.

(56) References Cited

U.S. PATENT DOCUMENTS

| | | | | |
|---|---|---|---|---|
| 5,059,415 A * | 10/1991 | Neuwelt | ............... | A61K 49/06 424/9.34 |
| 5,583,201 A | 12/1996 | Cameron, Sr. et al. | | |
| 6,589,746 B1 * | 7/2003 | Zemlan | ................. | C07K 16/18 424/130.1 |
| 7,741,446 B2 | 6/2010 | Pardridge et al. | | |
| 7,772,185 B2 | 8/2010 | English et al. | | |
| 2003/0040660 A1 | 2/2003 | Jackowski | | |
| 2006/0160184 A1 | 7/2006 | Mattheus-Hoogenboom | | |
| 2007/0053839 A1 | 3/2007 | Zhang | | |
| 2009/0155223 A1 * | 6/2009 | Kerr et al. | ................... | 424/93.7 |

OTHER PUBLICATIONS

Bendszus et al. "Caught in the Act: In Vivo Mapping of Macrophage Infiltration in Nerve Injury by Magnetic Resonance Imaging", The Journal of Neuroscience, Nov. 26, 2003 • 23(34):10892-10896.*
Wessig C. The Blood-Brain and Other Neural Barriers, Reviews and Protocols, New York Humana Press; Springer Science, Chapter 12.*
Document for anatomy classes in Indiana University—Purdue University Indianapolis, Nervous Tissue, Peripheral Nervous System (PNS); downloaded online on Mar. 1, 2016.*
Poduslo et al., Macromolecular permeability across the blood-nerve and blood-brain barriers, Proc. Natl. Acad. Sci. USA, vol. 91, pp. 5705-5709, Jun. 1994 Neurobiology.*
Chater et al., Erb's palsy—Who is to blame and what will happen, Paediatr Child Health 2004;9(8):556-560.*
Hiesiger et al., Opening the Blood-Brain and Blood-Tumor Barriers in Experimental Rat Brain Tumors: The Effect of Intracarotid Hyperosmolar Mannitol on Capillary permeability and Blood Flow, Ann Neurol 19:50-59, 1986.*
Seneviratne, Permeability of blood nerve barriers in the diabetic rat, Journal of Neurology, Neurosurgery, and Psychiatry, 1972, 35, 156-162.*
Mellick et al., Longitudinal movement of radioiodinated albumin within extravascular spaces of peripheral nerves following three systems of experimental trauma, J. Neurol. Neurosurg. Psychiat., 1967, 30, 458.*
Poduslo et al., Polyamine modification increases the permeability of the proteins at the blood-nerve and blood-brain barriers, J Neurochem. Apr. 1996;66(4):1599-609. (Year: 1996).*
Nolte et al: "Experimental nerve imaging at 1.5-T", Methods, Academic Press, Aug. 23, 2007, pp. 21-28, vol. 43, No. 1, XP22210954, ISSN: 1046-2023, University of Wurzburg, Germany.
European Search Report relating to EP Application No. 12847971.4 dated Jun. 11, 2015.

* cited by examiner

*Primary Examiner* — Robert A Wax
*Assistant Examiner* — Nabila G. Ebrahim
(74) *Attorney, Agent, or Firm* — Polsinelli PC

(57) ABSTRACT

An improved method for diagnosing and characterizing peripheral nerve lesions to permit early identification and characterization of peripheral nerve injuries that will require surgical intervention.

20 Claims, 2 Drawing Sheets

METHOD FOR DIAGNOSTICALLY IMAGING LESIONS IN THE PERIPHERAL NERVOUS SYSTEM

CROSS-REFERENCE TO RELATED APPLICATION

This patent application claims priority to U.S. Patent Application Ser. No. 61/558,805 filed Nov. 11, 2011 and titled Method For Diagnostically Imaging Lesions In The Peripheral Nervous System, the entire contents of which is incorporated herein by reference in its entirety.

BACKGROUND

1. Field

Embodiments of the present invention relate to diagnostic imaging. More particularly, embodiments of the present invention relate to a method to diagnose and characterize lesions in a peripheral nervous system.

2. Discussion of Related Art

Currently, in the setting of acute injury, there exists no method to reliably distinguish peripheral nerve injuries that will spontaneously resolve from those that will require surgical intervention to restore function. U.S. Pat. No. 5,059,415 to Neuwelt titled Method Of Diagnostically Imaging Lesions In The Brain Inside A Blood-Brain Barrier is incorporated by reference in its entirety. In some cases, the decision for surgery is made only after an observation period that can last several months. Early intervention translates to better functional outcomes.

Additionally, functional outcomes hinge on the ability of the regenerating nerve to reach its muscular target before motor end-plate demise. This irreversible denervation of the muscle occurs at approximately eighteen months. If diagnosis could be made immediately, surgical intervention could take place sooner; thereby increasing the likelihood the regenerating nerve will reach its target sooner, e.g., before eighteen months elapse. The length of time that elapses from time of injury to surgery is inversely proportional to the degree of functional recovery.

Accordingly, there is a need to provide a method for early identification and characterization of peripheral nerve injuries that will require surgical intervention to revolutionize the surgical management of peripheral nerve injuries.

(The following references are incorporated by reference in their entireties: Sunderland S. The anatomy and physiology of nerve injury. Muscle Nerve 1990; 13:771-84.) (Lee D K, Wolfe S W. Peripheral nerve injury and repair. J Am Acad Orthop Surg. 2000; 8(4):243-52.) (Johns R, Boppart S A. Magnetomotive molecular nanoprobes. Curr Med Chem. 2011; 18(14):2103-14.) (Luchetti A, Milani D, Ruffini F, Galli R, Falini A, Quattrini A, Scotti G, Comi G, Martino G, Furlan R, Politi L S. Monoclonal Antibodies Conjugated with Superparamagnetic Iron Oxide Particles Allow Magnetic Resonance Imaging Detection of Lymphocytes in the Mouse Brain. Mole Imagaing. 2011 Sep. 28.) (Birch R. Chapter 32—Nerve Repair. In, Wolfe S W, Hotchkiss R N, Pedereson W C, Kozin S H. Green's Operative Hand Surgery $6^{th}$ Ed., Elsevier, 2011.) (Spinner R J, Shin A Y, Hert-Blouin M N, Elhassan B T, Bishop A T. Chapter 38—Traumatic Brachial Plexus Injury. In, Wolfe S W, Hotchkiss R N, Pedereson W C, Kozin S H. Green's Operative Hand Surgery $6^{th}$ Ed., Elsevier, 2011.) (Waters, P M. Chapter 44—Pediatric Brachial Plexus Palsy. In, Wolfe S W, Hotchkiss R N, Pedereson W C, Kozin S H. Green's Operative Hand Surgery $6^{th}$ Ed., Elsevier, 2011.) (Neumaier C E, Baio G, Ferrini S, Corte G, Daga A. MR and iron magnetic nanoparticles. Imaging opportunities in preclinical and translational research. Tumori. 2008; 94:226-233.) (Mohler L R, Hanel D P. Closed Fractures Complicated by Peripheral Nerve Injury. J Am Acad Orthop Surg 2006; 14:32-37.) (Weerasuriya A, Mizisin A P. Chapter 6—The Blood-Nerve Barrier: Structure and Functional Significance. In, Sukriti N (ed.), The Blood-Brain and Other Neural Barriers: Reviews and Protocols, Methods in Molecular Biology, vol 686, Springer Science 2011.) (Wessig C. Chapter 12—Detection of Blood-Nerve Barrier Permeability by Magnetic Resonance Imaging. In, Sukriti N (ed.), The Blood-Brain and Other Neural Barriers: Reviews and Protocols, Methods in Molecular Biology, vol 686, Springer Science 2011.) (Grant G A, Goodkin R, Maravilla K R, Kliot M. MR Neurography: diagnostic utility in the surgical treatment of peripheral nerve disorders. Neuroimg Clin N Am 2004; 14:115-133.) Ecklund J M, Ling G S. From the battlefront: peripheral nerve surgery in modern day warfare. NeruosurgClin N Am. 2009 January; 20(1):107-110.vii. Review, and Kretschemer T, Heinen C W, Antonaiadis G, Richter H P, Konig R W. Iatrogenic nerve injuries. Neurosurg Clin N Am. 2009 Jan. 20(1):73-90, vii. Review, and Kozin S H. The evaluation and treatment of children with brachial plexus birth palsy. J Hand Surg Am. 2011 August; 36(8):1360-1369.)

SUMMARY

The following brief description is provided to indicate the nature of the subject matter disclosed herein. While certain aspects of the present inventive concept are described below, the summary is not intended to limit the scope of the present inventive concept. Embodiments of the present inventive concept provide a diagnostic imaging method. The present inventive concept does not suffer from and remedies the deficiencies of conventional methods such as those previously set forth herein.

The present inventive concept provides, in its simplest form, an improved method for diagnosing and characterizing peripheral nerve lesions to permit early identification and characterization of peripheral nerve injuries that will require surgical intervention.

The method provided by the present general inventive concept is advantageous over conventional methods for at least the reason that the method enables the accurate analysis of peripheral nerve lesions and the ability to distinguish lesions where the blood-nerve barrier ("BNB") remains intact, and therefore has greater self-regeneration potential from lesions where the connective tissue layers comprising the BNB are disrupted, and therefore require surgical intervention to obtain any meaningful neurological recovery. The present method represents an advance in the art of diagnosis of peripheral nerve lesions.

The aforementioned may be achieved in one aspect of the present invention by providing a method to diagnose and/or characterize peripheral nerve lesions. The method may include the step of introducing a chemical agent operable to bind directly to peripheral nerve lesions in which the blood-nerve barrier is compromised such that a target molecule is immune privileged and unavailable for interaction with the chemical agent unless the blood-nerve barrier is compromised. The target molecule is such that it is (i) not shielded in injured nerves or abnormal tissue via the blood-nerve barrier and/or (ii) shielded in uninjured nerves or normal tissue via the blood-nerve barrier. The target molecule is immune privileged and/or unavailable for interaction with the chemical agent unless the blood-nerve barrier is compromised. The method may also include the step of attaching a label to the chemical agent. The chemical agent with the label may be operable to localize in regions where a peripheral of the nerve-blood barrier is disrupted.

The method may also include the step of quantitatively analyzing the peripheral nerve or nerves to determine the amount of labeling agent present. The analyzing may be performed using magnetic resonance imaging techniques or the like. The chemical agent may be a monoclonal antibody. The chemical agent may also be operable to bind specifically and exclusively to the peripheral nerve lesions in which the blood-nerve barrier is compromised. The chemical agent that will localize at peripheral nerve lesions in which the blood-nerve barrier is compromised may be an antibody against an axonal protein.

The blood-nerve barrier may be compromised by neurotmesis. The label attached to the chemical may be gadolinium-DTPA or superparamagnetic iron oxide nanoparticles. The method may enable the accurate analysis of peripheral nerve lesions and the ability to distinguish axonotmetic lesions with greater self-regeneration potential from neurtmetic lesions that may require intervention.

Additional aspects, advantages, and utilities of the present inventive concept will be set forth in part in the description which follows and, in part, will be obvious from the description, or may be learned by practice of the present inventive concept.

BRIEF DESCRIPTION OF THE DRAWINGS

Embodiments of the present inventive concept are described in detail below with reference to the attached drawing figures, wherein.

Figure 1:
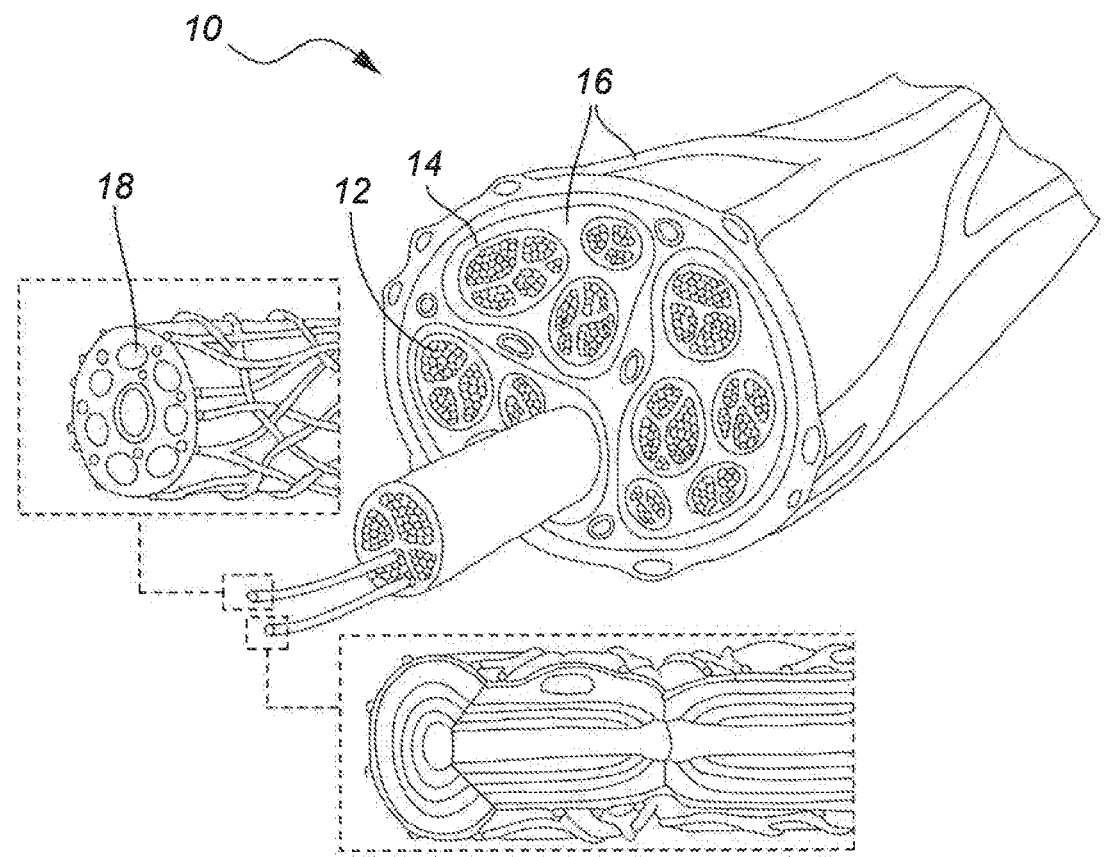
FIG. 1 is a magnified perspective view illustrating a peripheral nerve.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

The present general inventive concept relates to blood-nerve barrier permeability, which correlates with suboptimal neurological recovery via spontaneous regeneration alone, and can be demonstrated in an acute peripheral nerve injury. Detection of blood-nerve barrier permeability permits identification of traumatic peripheral nerve lesions indicated for surgical repair.

Figure 2:
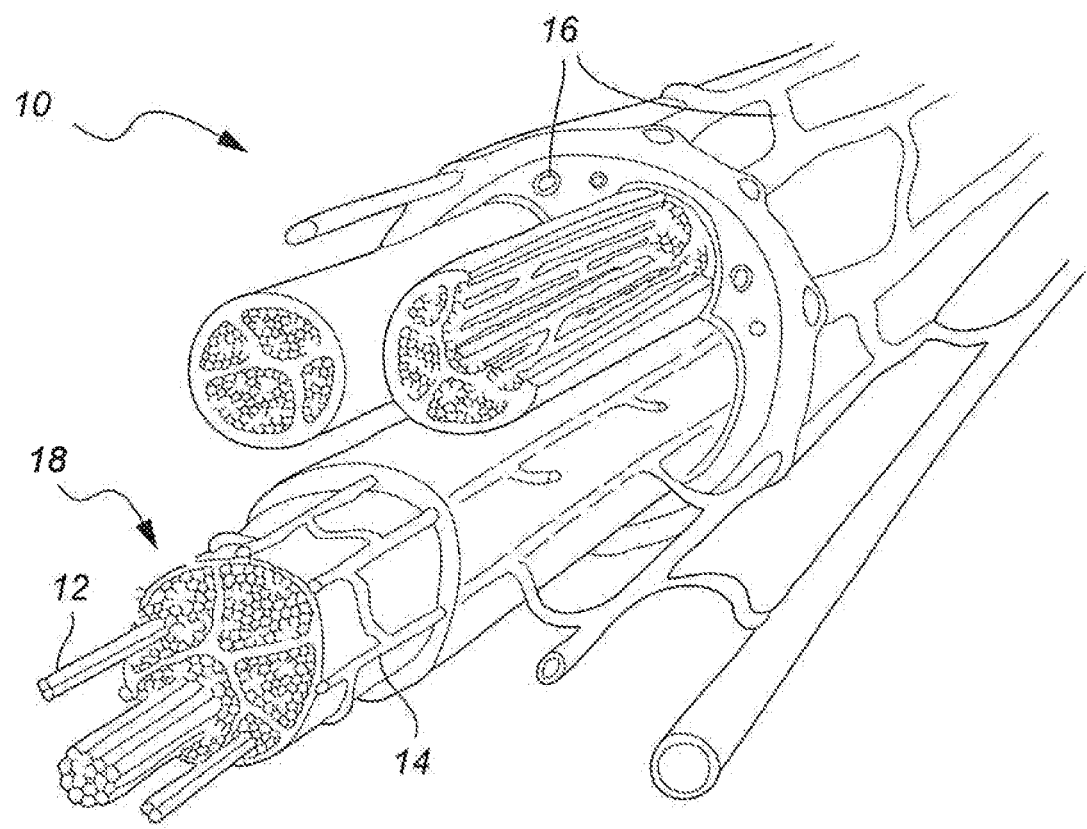
FIG. 2 is a magnified perspective view illustrating a peripheral nerve.

Understanding the cross-sectional anatomy of a peripheral nerve is critical to understanding the classification of nerve injuries, and what differentiates those injuries that will spontaneously regenerate to those that require surgical intervention. FIGS. 1 and 2 illustrate a peripheral nerve 10 having three layers of connective tissue, i.e., the endoneurium 12, the perineurium 14, and the epineurium 16, surrounding axons 18, which, in combination, form the peripheral nerve 10.

The axons 18 are long extensions operable to transmit action potentials from a cell body to its target organ. The axons 18 each, individually, travel through a collagenous matrix known as the endoneurium 12. Bundles of the axons 18 form fascicles, each surrounded by the perineurium 14. The epineurium 16 encircles the perineurium 14 and also forms an outermost sheath of the peripheral nerve 10. The endoneurium 12, the perineurium 14, and the epineurium 16 serve varied functions, and the patterns of any injury to these layers of connective tissue 12, 14, 16 correlate with the severity of the peripheral nerve injury.

The perineurium 14 along with the capillaries of the endoneurium 12 provide a blood-nerve interface, or blood-nerve barrier ("BNB") 18. The BNB 18 is a diffusion barrier that functions as an immunologically and biochemically privileged territory. This BNB 18 has properties similar to the blood-brain barrier in the central nervous system. Endothelial cells within the capillaries of the endoneurium are interconnected with tight junctions that create a system impermeable to a wide range of macromolecules, e.g., proteins.

Classification systems for injuries to the peripheral nerve 10 have been described in anatomic terms, and describe structures that are disrupted. As illustrated in Table 1, i.e., Sunderland's classification, the endoneurium 12 remains intact in Type 1 & 2 injuries. Thus, even if the axon is transected as in Type 2 lesions, the regenerating axon will reach its target end organ, guided by an intact endoneurial tube. Surgery is required for Type 4 and 5 lesions, where the endoneurium 12 and perineurium 14 are disrupted, and the BNB 18 is compromised.

TABLE 1

| Injury Classification | | |
|---|---|---|
| Seddon[2] | Sunderland[1] | Pathophysiologic Features |
| Neurapraxia | Type 1 | Local myelin damage usually secondary to compression |
| Axonotmesis | Type 2 | Loss of continuity of axons; endoneurium, perineurium, and epineurium intact |
| | Type 3 | Loss of continuity of axons and endoneurium; perineurium and epineurium intact |
| | Type 4 | Loss of continuity of axons, endoneurium, and perineurium; epineurium intact |
| Neurotmesis | Type 5 | Complete physiologic disruption of entire nerve trunk |

The method includes the initial step of introducing a chemical agent, e.g., monoclonal antibody, which binds directly, specifically and exclusively to peripheral nerve lesions in which the BNB 18 is compromised or relatively more permeable, e.g., antibody with binding affinity to an axonal protein. The target molecule with which this chemical agent interacts, e.g., epitope, is found within the BNB 18 in normal tissue. In normal tissue, the target molecule is unavailable for interactions with the chemical agent, e.g., antibody, because the chemical agent does not readily cross the BNB 18. Wherever the BNB 18 is compromised, the chemical agent will interact with the target molecule, thereby localizing to the specific site of the BNB 18 permeability.

The chemical agent must be detectable by either its inherent properties or via a labeling agent. For example, monoclonal antibodies are not readily detectable, but become so once a label is attached thereto, e.g., gadolinium-DTPA, or superparamagnetic iron oxide nanoparticles. The chemical agent and label localize and accumulate at sites where the BNB 18 is disrupted or permeable.

The chemical agent utilized is one that does not readily cross the intact BNB 18, yet interacts specifically with a target that lies behind the BNB 18 in normal tissue and will localize to sites of BNB 18 permeability. The chemical agent is preferably a monoclonal antibody, and it is foreseen may be any binding protein or any such macromolecule that is operable to bind to a specific target, yet does not readily cross the BNB 18 in normal tissue without deviating from the scope of the present inventive concept.

Upon localization of the chemical agent at sites of the BNB 18, it is necessary to attempt to detect the chemical agent. Thus, the peripheral nerve or nerves are analyzed to determine the presence and/or amount of chemical agent by detection of its labeling agent. Detection methods may include, but are not limited to various imaging modalities, preferably, though not limited to magnetic resonance imaging techniques. For example, a monoclonal antibody will not readily cross the BNB 18, though it can be designed to target and interact exclusively with a protein that is normally behind the BNB 18. This antibody may be labeled with a magnetic resonance imaging contrast agent that will be detected at sites of peripheral nerve injuries that demonstrate blood-nerve barrier permeability.

It is foreseen that the chemical agent could act as a therapeutic as well as diagnostic agent by targeting and inhibiting the action of a molecule that normally hinders nerve regeneration.

The method of the present inventive concept may be utilized in various clinical applications including, but not limited to, the following.

In brachial plexus birth palsy, the regeneration potential of peripheral nerve injuries in some way depends on the integrity of the endoneurium 12 and/or BNB 18. The current method of differentiating injuries that will regenerate, e.g., axonotmetic injuries, with those that require surgical intervention to repair, e.g., neurotmetic injury, is an observation period that might last several months, e.g., a three to six month observation period. Functional outcome hinges on the ability of the regenerating nerve to reach its muscular target before motor end-plate demise occurs. Irreversible dennervation of the muscle occurs at approximately eighteen months. Because the method of the present inventive concept facilitates an immediate or at least expedited diagnose, surgical intervention can take place sooner, thereby increasing the likelihood the regenerating nerve will reach its target before eighteen months elapse.

Gunshot injuries ("GSI") present another dilemma in management. A considerable number of post-GSI nerve injuries will spontaneously resolve, so a period of observation is often instituted to determine which patients are indicated for surgical intervention. This may equate to loss of critical nerve regeneration time. The method of the present general inventive concept is able to identify those patients in whom surgical exploration and intervention is indicated, thereby avoiding any loss of critical nerve regeneration time.

In Iatrogenic nerve injuries, nerve injuries sustained in surgery or due to injections are also often observed for a period of time to differentiate which patients have a transient neuropraxia or axonometic injury versus those who have a neurotmetic injury and therefore require surgical intervention.

Lastly, the method of the present inventive concept may be used to diagnose nerve injury related to closed injuries, such as fractures, that will require surgical repair.

Accordingly, the present general inventive concept provides a method for diagnostically imaging of lesions in a peripheral nervous system that is superior to conventional methods for at least the reasons described herein.

Having now described the features, discoveries and principles of the general inventive concept, the manner in which the general inventive concept is constructed and used, the characteristics of the construction, and advantageous, new and useful results obtained; the new and useful structures, devices, tools, elements, arrangements, parts and combinations, are set forth in the appended claims.

It is also to be understood that the following claims are intended to cover all of the generic and specific features of the general inventive concept herein described, and all statements of the scope of the general inventive concept, which, as a matter of language, might be said to fall therebetween.

What is claimed is:

1. A method to characterize peripheral nerve lesions by detecting blood-nerve barrier permeability, the method including the steps of:
   introducing a chemical agent to a peripheral nerve having a blood-nerve barrier to characterize peripheral nerve lesions, the chemical agent operable to interact with an epitope within the blood-nerve barrier,
   detecting blood-nerve barrier permeability by analyzing the peripheral nerve to detect an amount of the chemical agent at a site of the blood-nerve barrier permeability, the blood-nerve barrier permeability caused by a lesion,
   wherein,
      the chemical agent (i) does not interact with the epitope unless the blood-nerve barrier is permeable and allows the epitope to be exposed to the chemical agent, and (ii) is operable to localize at the site of the blood-nerve barrier permeability, and
      the method does not include modification of the blood-nerve barrier permeability.

2. The method of claim 1, further comprising the step of:
   attaching a label to the chemical agent,
   wherein,
      the chemical agent is operable to localize in regions where the blood-nerve barrier is disrupted.

3. The method of claim 2,
   wherein the analyzing of the peripheral nerve includes determining the amount of the chemical agent present in the peripheral nerve.

4. The method of claim 3,
wherein,
the analyzing of the peripheral nerve is performed using magnetic resonance imaging, and
the label has a magnetic resonance imaging contrast agent.

5. The method of claim 1,
wherein the chemical agent is a monoclonal antibody.

6. The method of claim 1,
wherein the chemical agent is operable to bind exclusively to the peripheral nerve lesions.

7. The method of claim 1,
wherein the chemical agent is an antibody against an axonal protein.

8. The method of claim 1,
wherein the blood-nerve barrier is permeable due to neurotmesis.

9. A method to diagnose a nerve injury using a chemical agent having a label by detecting permeability of a blood-nerve barrier of a peripheral nerve, the method including the steps of:
introducing the chemical agent having the label to the blood-nerve barrier, the chemical agent operable to bind to an epitope exposed at a permeable site of the blood-nerve barrier; and
detecting blood-nerve barrier permeability by imaging the peripheral nerve using magnetic resonance imaging to determine a presence of the chemical agent at the permeable site of the blood-nerve barrier, the blood-nerve barrier permeability caused by an injury,
wherein,
the label is (i) attached to the chemical agent, (ii) a contrast agent, and (iii) operable to localize and be detected at peripheral nerve injury sites that demonstrate blood-nerve barrier permeability via the magnetic resonance imaging.

10. The method of claim 1,
wherein the method enables accurate analysis of the peripheral nerve lesions and the ability to distinguish axonotmetic lesions with greater self-regeneration potential from neurotmetic lesions that may require intervention.

11. The method of claim 9,
wherein,
the permeable site of the blood-nerve barrier is a disruption in the blood-nerve barrier, and
the chemical agent is operable to localize in regions where the blood-nerve barrier is disrupted.

12. The method of claim 1,
wherein,
the lesion features (i) a loss of axons, and (ii) disruption of endoneurium and perineurium.

13. The method of claim 1,
wherein,
the lesion is a neurotmetic lesion or related to birth palsy.

14. The method of claim 9,
wherein,
the permeable site of the blood-nerve barrier is caused by a lesion.

15. The method of claim 14,
wherein,
the lesion features (i) a loss of axons, and (ii) disruption of endoneurium and perineurium.

16. The method of claim 14,
wherein,
the injury is a neurotmetic injury or related to birth palsy.

17. The method of claim 9,
wherein,
the method does not include modification of permeability of the blood-nerve barrier.

18. The method of claim 9,
wherein,
the method enables accurate analysis of peripheral nerve lesions and ability to distinguish axonotmetic lesions with greater self-regeneration potential from neurotmetic lesions that may require intervention.

19. The method of claim 9,
wherein,
the label is gadolinium-DTPA or superparamagnetic iron oxide nanoparticles.

20. In a peripheral nerve having connective tissue layers comprising a blood-nerve barrier that normally protects an epitope within the blood-nerve barrier from interaction with a chemical agent outside the blood-nerve barrier, a method for distinguishing peripheral nerve lesions in which the blood-nerve barrier remains intact from other peripheral nerve lesions in which the blood-nerve barrier has been disrupted to become permeable, the method comprising the steps of:
providing a quantity of the chemical agent that normally does not cross an intact blood-nerve barrier of the peripheral nerve, the chemical agent operable to interact with the epitope within the blood-nerve barrier if the blood-nerve barrier has been disrupted to become permeable thereby permitting the chemical to cross the blood-nerve barrier, the chemical agent operable to localize at a site where the blood-nerve barrier has become permeable;
introducing the chemical agent to the blood-nerve barrier;
allowing the chemical agent to cross the blood-nerve barrier at a peripheral nerve site where the blood-nerve barrier has become permeable and allowing the chemical agent to bind with the epitope at the peripheral nerve site; and
detecting an amount of the chemical agent at the peripheral nerve site to characterize severity of a peripheral nerve lesion.

* * * * *